(12) United States Patent
Umezawa et al.

(10) Patent No.: US 8,178,135 B2
(45) Date of Patent: May 15, 2012

(54) AQUEOUS SOLUTION OF CONOPHYLLINE AND/OR CONOPHYLLIDINE

(75) Inventors: Kazuo Umezawa, Kanagawa (JP); Mikio Fujii, Tokyo (JP)

(73) Assignee: Keio University, Tokyo (JP)

( * ) Notice: Subject to any disclaimer, the term of this patent is extended or adjusted under 35 U.S.C. 154(b) by 602 days.

(21) Appl. No.: 12/281,940

(22) PCT Filed: Mar. 5, 2007

(86) PCT No.: PCT/JP2007/054195
§ 371 (c)(1), (2), (4) Date: Jun. 4, 2009

(87) PCT Pub. No.: WO2007/102467
PCT Pub. Date: Sep. 13, 2007

(65) Prior Publication Data
US 2010/0286184 A1 Nov. 11, 2010

(30) Foreign Application Priority Data
Mar. 7, 2006 (JP) .................................. 2006-060533

(51) Int. Cl.
*A61K 36/00* (2006.01)
(52) U.S. Cl. ....................................................... 424/725
(58) Field of Classification Search .................. 424/725; 514/183, 279
See application file for complete search history.

(56) References Cited

U.S. PATENT DOCUMENTS
2007/0232533 A1 10/2007 Umezawa et al.
2009/0239301 A1 9/2009 Umezawa et al.
2009/0291153 A1 11/2009 Umezawa et al.

FOREIGN PATENT DOCUMENTS
| EP | 1772066 A1 * | 4/2007 |
| JP | 9-67377 | 3/1997 |
| JP | 10-45763 | 2/1998 |
| JP | 2000-226330 | 8/2000 |
| JP | 2003-171294 | 6/2003 |
| WO | WO 2004/024070 | 3/2004 |
| WO | WO 2004/050058 | 6/2004 |
| WO | WO 2004/099215 | 11/2004 |
| WO | WO 2005/099485 | 10/2005 |

OTHER PUBLICATIONS

English language translation of Matsumoto et al. ed., "Yakuzaigaku Manual," 1st edition, Mar. 20, 1989, p. 29.
English language translation of Okano ed., "Shin Yakuzaigaku Soron," Revised Edition No. 3, Apr. 10, 1987, pp. 177-178 and 257-260.
Kam et al., "Conophylline and Conophyllidine: New Dimeric Alkaloids from *Tabernaemontana divaricata*," *J. Nat. Prod.* 56(11):1865-1871 (1993).
Matsumoto et al. ed., "Yakuzaigaku Manual," 1st edition, Mar. 20, 1989, p. 29.
Ogata et al., "Promotion of β-Cell Differentiation by Conophylline in Fetal and Neonatal Rat Pancreas," *Diabetes* 53:2596-2602 (2004).
Umezawa et al., "Induction of Insulin Production in Rat Pancreatic Acinar Carcinoma Cells by Conophylline," *Biomed. Pharmacother.* 57:341-350 (2003).
Okano ed., "Shin Yakuzaigaku Soron," Revised Edition No. 3, Apr. 10, 1987, pp. 177-178 and 257-560.
International Search Report for International Application PCT/JP2007/054195, mailed Apr. 10, 2007.

* cited by examiner

*Primary Examiner* — Kevin E Weddington
(74) *Attorney, Agent, or Firm* — Clark & Elbing LLP

(57) ABSTRACT

PROBLEMS TO BE SOLVED BY THE INVENTION
To provide aqueous solutions of conophylline and/or conophyllidine; methods for purifying conophylline and/or conophyllidine from the aqueous solutions; methods for producing the aqueous solutions, water-soluble compositions containing conophylline and/or a conophyllidine useful for food compositions or pharmaceutical compositions or methods for preparing the same; as well as food compositions or pharmaceutical compositions containing the water-soluble compositions.
MEANS OF SOLVING THE PROBLEMS
It has been found that conophylline and/or conophyllidine can be efficiently extracted from a plant producing conophylline and/or conophyllidine with an acidic aqueous solution having a pH equal to or less than 4. The extract thus obtained, i.e., aqueous solution of conophylline, and/or conophyllidine is useful for production of, for instance, food compositions, pharmaceutical compositions, etc.

3 Claims, 4 Drawing Sheets

US 8,178,135 B2

AQUEOUS SOLUTION OF CONOPHYLLINE AND/OR CONOPHYLLIDINE

CROSS-REFERENCE TO RELATED APPLICATIONS

The present application is the U.S. National Stage of International Application No. PCT/JP2007/054195, filed Mar. 5, 2007, which claims the benefit of Japanese Patent Application Serial No. 2006-060533, filed Mar. 7, 2006, which is incorporated herein by reference.

TECHNICAL FIELD

The present invention relates to aqueous solutions of conophylline and/or conophyllidine or method for purifying conophylline and/or conophyllidine; methods for producing the aqueous solutions; water-soluble compositions containing conophylline and/or conophyllidine useful for food compositions or pharmaceutical compositions or methods for producing the water-soluble compositions; and food compositions or pharmaceutical compositions containing the water-soluble compositions.

BACKGROUND ART

Diabetes is categorized into two types: type 1 diabetes, which is caused by destruction of pancreatic β cells and develops at younger ages, and type 2, which is a lifestyle-related disease and is common in older ages. In either type, once diabetes develops, the patient must undergo continued lifelong symptomatic treatment including diet therapy, exercise therapy, hypoglycemic medication (oral agents or insulin injection). No radical therapy for diabetes is available and the target population is expected to increase steadily in the future.

Before the onset of diabetes, insufficiency of insulin secretion or decreased insulin function (insulin resistance) is often found. It is particularly important in suppressing the onset of diabetes to maintain adequate insulin producing ability at the pre-onset stage. The main purpose of diabetic pharmaceuticals is, however, to suppress hyperglycemia accompanying the onset of diabetes and to eliminate the factor for diabetic complications; no treatment method for eliminating the fundamental cause of diabetes has been established. Moreover, although a wide variety of health foods aiming at prevention and/or risk reduction of diabetes are available in the market, their effect is to suppress the postprandial hyperglycemia, which does not lead to elimination of the fundamental cause.

Although regeneration of insulin-producing β cells can potentially be a radical therapy and have a preventive effect, the current researches in this field which have yielded practical results as the method for regenerating β cells present the approaches taking advantage of organ or cell transplantation, or gene therapy. Such approaches should inevitably depend on organ transplantation surgery, injections of biological macromolecules (protein), etc., thereby imposing a great burden on patients and markedly deteriorating their quality of life (QOL). Thus, compositions capable of activating regeneration of an organ, especially pancreatic β cells, by oral administration, have been desired.

It is conventionally known that substances such as conophylline and conophyllidine (Anticancer Res. vol. 14: p. 413-2418, 1994; and J. Nat. Prod. vol. 56: p. 1865-1871, 1993) activate regeneration of pancreatic β cells (Biomed. Pharmacol. vol. 57: p. 341-350, 2003). Further, it is known that conophylline has a function of significantly suppressing increased blood glucose levels when intraperitoneally administered to model animals of neonatal diabetes (Diabetes vol. 53: p. 2596-2602, 2004).

Further, conophylline is considered to be useful in increasing insulin-producing ability and/or insulin-secreting ability of non-neoplastic cells derived from the pancreas, preventing and/or treating a disease associated with lack of insulin, reducing blood glucose levels, inducing differentiation of non-neoplastic cells derived from the pancreas into insulin-producing cells, and so forth (WO 04/099215). Moreover, since leaves of conophylline-producing plants or their dried product, their extracts, etc. induce AR42J cells to differentiate into insulin-producing cells and/or reduce blood glucose levels, they are considered to be useful as health foods for preventing or improving diabetes and/or reducing blood glucose levels (WO05/099485).

Because of their low water solubility, however, these substances are extracted with an organic solvent, making it difficult to prepare an aqueous solution of conophylline and/or conophyllidine suitable for oral administration.

DISCLOSURE OF THE INVENTION

Problems to be Solved by the Invention

Thus, the object of the present invention is to provide aqueous solutions of conophylline and/or conophyllidine; methods for purifying conophylline and/or conophyllidine from the aqueous solutions; methods for producing the aqueous solutions; water-soluble compositions containing conophylline and/or conophyllidine useful for food composition or pharmaceutical composition or methods for preparing the water-soluble compositions; and food compositions or pharmaceutical compositions containing the water-soluble compositions.

Means for Solving the Problems

The inventors have assiduously studied to obtain aqueous solutions of conophylline and/or conophyllidine whose usage forms can easily be changed, and found that aqueous solutions of conophylline or conophyllidine can be produced by extracting *Tabernaemontana divaricata* with an acidic aqueous solution and neutralizing the extract. In particular, the inventors have revealed that by once treating the extract with an acidic aqueous solution having a pH equal to or less than 4, aqueous solutions in which conophylline or conophyllidine is dissolved in a concentration of 2 μg/ml or higher, which have conventionally been impossible, can be produced.

However, conophylline and/or conophyllidine partially purified could be dissolved in an acidic aqueous solution, but precipitated for the most part when the acidic aqueous solution was neutralized. The inventors have found that when the aforementioned extract prepared with an acidic aqueous solution is size-fractionated at molecular weight of 10000 and then fractions corresponding to low molecular weights are neutralized, most of the conophylline and/or conophyllidine precipitates; whereas when an extract prepared from the aforementioned pulverized product with an acidic aqueous solution is neutralized and then is size-fractionated at molecular weight of 50000, most of the conophylline and/or conophyllidine remains unprecipitated. This suggests that macromolecules contained in dried leaves of *Tabernaemontana divaricata* is involved in the dissolution of conophylline and/or conophyllidine. As a result of diligent study, the inventors have found that an anionic water-soluble macromolecule having a carboxyl group is one of such macromolecules.

Further, the inventors have found that when a crude extract obtained by drying an ethanol extract of dried leaves of a plant that produces conophylline and/or conophyllidine is orally administered to diabetic model rats as a suspension in a hydrophilic solvent, conophylline and/or conophyllidine is absorbed into blood, is maintained stably in blood for a certain period of time, significantly increase the number of pancreatic β cells and blood insulin levels, and significantly reduce blood glucose levels which have been elevated by the onset of diabetes. Thus, the inventors have completed the present invention.

Accordingly, the aqueous solution according to the present invention is an aqueous solution of conophylline and/or conophyllidine. It is preferred that in this aqueous solution conophylline and/or conophyllidine is dissolved at a concentration of 2 μg/ml or higher.

The method for producing an aqueous solution of conophylline and/or conophyllidine according to the present invention includes the step of dissolving an anionic water-soluble macromolecule with a carboxyl group in an acidic aqueous solution having a pH equal to or less than 4 containing conophylline and/or conophyllidine.

Further, the method for producing an aqueous solution of conophylline and/or conophyllidine according to the present invention includes the step of dissolving conophylline and/or conophyllidine in a hydrophilic solvent containing a surface active agent.

Further, the method for producing an aqueous solution of conophylline and/or conophyllidine according to the present invention includes the step of preparing an extract from a plant producing conophylline and/or conophyllidine with an acidic aqueous solution having a pH equal to or less than 4.

Further, the method for producing an aqueous solution of conophylline and/or conophyllidine according to the present invention includes the step of neutralizing an extract of a plant producing conophylline and/or conophyllidine, prepared with an acidic aqueous solution having a pH equal to or less than 4.

The aqueous solution according to the present invention is an aqueous solution of conophylline and/or conophyllidine obtained by the aforementioned method for producing an aqueous solution of conophylline and/or conophyllidine.

The method for purifying conophylline and/or conophyllidine according to the present invention includes the fractionation step of fractionating an extract of a plant producing conophylline and/or conophyllidine prepared with an acidic aqueous solution having a pH equal to or less than 4 at molecular weight of 10000 and the recovery step of recovering a low-molecular-weight fraction obtained by the fractionation step. It should be noted that, in the method for purifying conophylline and/or conophyllidine according to the present invention, a precipitate precipitated by neutralizing the aforementioned low-molecular-weight fraction may be recovered.

The method for purifying conophylline and/or conophyllidine according to the present invention includes the neutralization step of neutralizing an extract of a plant producing conophylline and/or conophyllidine prepared with an acidic aqueous solution having a pH equal to or less than 4, the fractionation step of fractionating the extract of the plant producing conophylline and/or conophyllidine prepared with an acidic aqueous solution having a pH equal to or less than 4 at molecular weight of 50000, and the recovery step of recovering a high-molecular-weight fraction obtained by the fractionation step.

The water-soluble composition according to the present invention is a water-soluble composition containing conophylline and/or conophyllidine, from which an aqueous solution of conophylline and/or conophyllidine, having a concentration of 2 μg/ml or higher, can be prepared. Further, the water-soluble composition according to the present invention contains conophylline and/or conophyllidine and an anionic water-soluble macromolecule with a carboxyl group. Moreover, the water-soluble composition according to the present invention contains conophylline and/or conophyllidine and a surface active agent.

The method for producing the water-soluble composition according to the present invention includes the step of preparing an acidic aqueous solution or a neutral aqueous solution of conophylline and/or conophyllidine having a concentration of 2 μg/ml or higher, the step of obtaining powder by drying the aforementioned acidic aqueous solution or neutral aqueous solution, and other procedures. Further, the method for producing the water-soluble composition according to the present invention includes the step of dissolving an anionic water-soluble macromolecule having a carboxyl group in an acidic aqueous solution having a pH equal to or less than 4 containing conophylline and/or conophyllidine. Moreover, the method for producing the water-soluble composition according to the present invention includes the step of dissolving conophylline and/or conophyllidine in a hydrophilic solvent containing a surface active agent.

The food composition and a pharmaceutical composition according to the present invention contain the above-described water-soluble composition. The food composition according to the present invention constitutes a health food, a functional food, a food for specified health uses, or the like. The pharmaceutical composition according to the present invention constitutes a preparation for oral administration.

It should be noted that the aforementioned water-soluble composition is useful, for example, to grow β cells, reduce blood glucose levels, elevate insulin levels, prevent or improve diabetes, and the like.

The aforementioned plant to be used is exemplified by, for example, *Tabernaemontana divaricata* or the like.

BEST MODE FOR CARRYING OUT THE INVENTION

Figure 1:
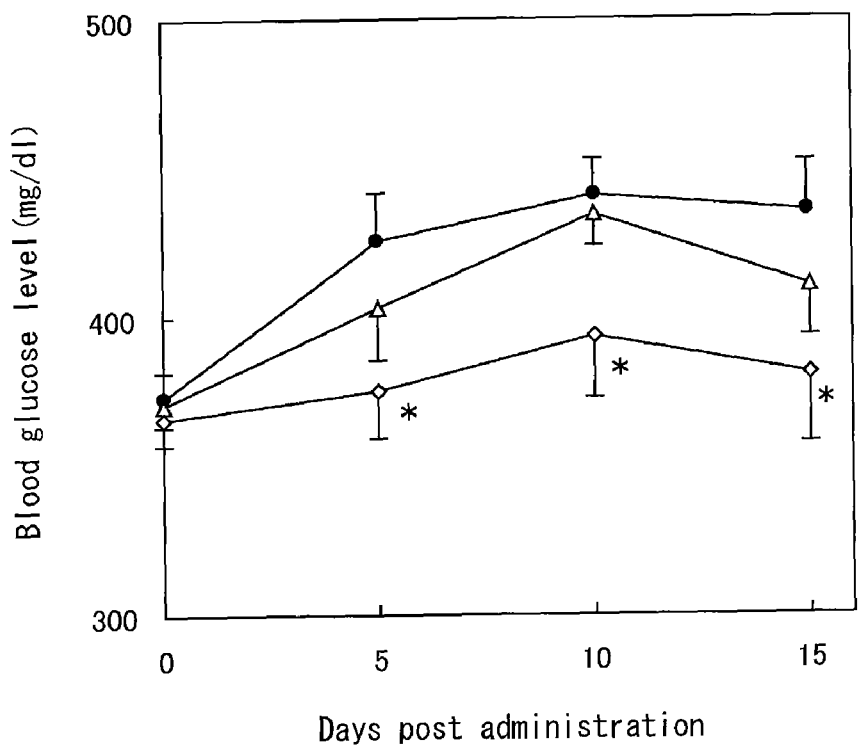
FIG. 1 is a graph showing the changes in blood glucose levels when Crude extract I was continually administered to STZ rats in one embodiment of the present invention. The black circles, white triangles, and white diamonds denote the mean of the control group, 50 mg/kg/day-administered group, and a 200 mg/kg/day-administered group, respectively, and vertical lines show standard errors. The asterisks indicate having statistical significance of 5% relative to the control group. The number of the animals used in each group is eight.

Embodiments of the present invention accomplished based on the above-described findings are hereinafter described in detail by giving Examples. When using commercial reagent kits and measuring apparatus, unless otherwise explained, attached protocols to them are used.

The object, characteristics, and advantages of the resent invention as well as the idea thereof will be apparent to those skilled in the art from the descriptions given herein. It is to be understood that the embodiments and specific examples of the invention described herein below are to be taken as preferred examples of the present invention. These descriptions are only for illustrative and explanatory purposes and are not intended to limit the invention to these embodiments or examples. It is further apparent to those skilled in the art that various changes and modifications may be made based on the descriptions given herein within the intent and scope of the present invention disclosed herein.

==Aqueous Solutions of Conophylline and/or Conophyllidine==

Basically, conophylline or conophyllidine hardly dissolves in a neutral aqueous solution. However, when the following two conditions are satisfied, conophylline or conophyllidine dissolves in a neutral aqueous solution at a high concentration:

(1) Conophylline or conophyllidine is once dissolved in acidic aqueous solution.
(2) Anionic water-soluble macromolecules having a carboxyl group is dissolved in the acidic aqueous solution in which conophylline or conophyllidine is dissolved.

For example, in order to obtain an extract containing conophylline and/or a conophyllidine as a principal component from green leaves or their dried product of a plant producing conophylline and/or a conophyllidine, the extraction may be performed with water. However, since a neutral aqueous solution cannot easily dissolve conophylline or conophyllidine, water extraction is inefficient and unpractical. However, by using an acidic aqueous solution having a pH equal to or less than 4 as described above, conophylline and/or conophyllidine can be efficiently extracted from green leaves or their dried product of a plant producing conophylline and/or a conophyllidine, and an aqueous solution of conophylline and/or conophyllidine, in which conophylline and/or conophyllidine is dissolved at a concentration of 2 µg/ml or higher, can be prepared. For example, almost all of the conophylline and/or a conophyllidine is present in a supernatant obtained by neutralizing and centrifuging the extract of a conophylline and/or conophyllidine-producing plant prepared with an acidic aqueous solution having a pH equal to or less than 4.

An extract prepared with ethanol from green leaves or their dried product of a plant producing conophylline and/or a conophyllidine, followed by removal of ethanol, cannot be dissolved in a neutral aqueous solution, but can be dissolved in an acidic aqueous solution having a pH equal to or less than 4. Thus, an aqueous solution of conophylline and/or conophyllidine can be prepared.

Further, by neutralizing the acidic aqueous solution having a pH equal to or less than 4 containing conophylline and/or conophyllidine prepared as described above, an aqueous solution of conophylline and/or conophyllidine having a pH around neutral can be prepared. When this aqueous solution is size-fractionated at molecular weight of 50000, almost all the conophylline and/or conophyllidine is separated into the high-molecular-weight fraction, suggesting that anionic water-soluble macromolecules having a carboxyl group is supplied from the leaves of the plant.

When (partially) purified conophylline or conophyllidine is once dissolved in an acidic aqueous solution and then neutralized, it can hardly dissolve in the solution. For example, when the extract prepared with the above-mentioned acidic aqueous solution having a pH equal to or less than 4 is size-fractionated at molecular weight of 10000 before being neutralized and then the resulting low-molecular-weight fraction is neutralized, most of the conophylline and/or conophyllidine is precipitated. Therefore, by dissolving an anionic water-soluble macromolecule having a carboxyl group (for example, polyuronic acids, such as pectin, polyacrylic acid, alginic acid, etc.) in an acidic aqueous solution having a pH equal to or less than 4 containing (partially) purified conophylline and/or (partially) purified conophyllidine, like the low-molecular-weight fraction obtained by fractionation using a membrane having a molecular weight cut-off of 10000, a high-concentration aqueous solution of conophylline and/or conophyllidine can be prepared at a pH around neutral.

Further, by dissolving conophylline and/or a conophyllidine in a hydrophilic solvent containing a surface active agent (e.g., sodium dodecyl sulfate (SDS), polyoxyethylene sorbitan fatty acid ester, (poly)glycerine fatty acid ester, sucrose fatty acid ester, etc.), an aqueous solution with a high-concentration of conophylline and/or conophyllidine can be prepared irrespective of pH.

Since the aqueous solution of conophylline and/or the conophyllidine prepared as described above does not contain any organic solvent, it is excellent in terms of safety and thus shows promise for use in food and pharmaceuticals.

It should be noted that the aforementioned hydrophilic solvent is exemplified by pure water, acidic aqueous solutions, etc. The acidic aqueous solutions include, for example, known aqueous solutions, such as hydrochloric acid, sulfuric acid, nitric acid, acetic acid, phosphoric acid, citric acid, etc. To increase the extraction efficiency of conophylline or conophyllidine, it is preferred to use an acidic aqueous solution having a pH equal to or less than 4; and it is more preferred to use hydrochloric acid or citric acid considering the flavor of the extract prepared with the acidic aqueous solution. It should be noted that when using hydrochloric acid or another strong acid, it is preferred to use an acid whose normality is 0.01 to 1 N, more preferably 0.02 to 0.2 N. In addition, when using an organic acid (weak acid), citric acid solution at 0.01 mol/liter or more, acetic acid at 0.03 mol/liter or more, or the like can be used.

Preferred examples of the aforementioned plant producing conophylline and/or a conophyllidine include Ervatamia microphylla, *Tabernaemontana divaricata*, etc., which are Apocynaceae family plants. Ervatamia microphylla can be harvested for example in Thailand and *Tabernaemontana divaricata* can be harvested for example in Southeast Asia, Japan, etc.

The dried product, including dried powder, of leaves of the aforementioned plants can be obtained by drying the leaves or pulverized leaves of the aforementioned plant using procedures such as air drying, freeze drying, warm air drying, et., or by drying and pulverizing leaves of the aforementioned plants. This pulverization can be performed with known apparatus such as a home mill, a mixer, or the like.

It should be noted that in extraction of conophylline or conophyllidine using the above-mentioned acidic aqueous solution having a pH equal to or less than 4, a small amount of ethanol may be added to the acidic aqueous solution, and heat (preferably 30 to 50° C.) may be applied to the acidic aqueous solution. Such treatment can increase extraction efficiency.

==Method for Purifying Conophylline and/or Conophyllidine==

Conophylline and/or a conophyllidine can be efficiently purified by taking advantage of the characteristics of conophylline and/or conophyllidine described so far. For example, after an extract of a plant producing conophylline and/or conophyllidine, which has been prepared with an acidic aqueous solution having a pH equal to or less than 4 without fractionation (e.g., by a known method such as ultrafiltration, gel filtration, or the like), is size-fractionated at molecular weight of 10000, the low-molecular-weight fraction obtained may be neutralized and the precipitate may be recovered by a known separation method (e.g., the centrifuge method, filtration method using filter paper or a filter cloth, or the like). Alternatively, the aforementioned extract, after being neutralized, may be size-fractionated at molecular weight of 50000 and the high-molecular-weight fraction obtained may be recovered.

==Water-Soluble Compositions of Conophylline and/or Composition==

By being orally administered, the aqueous solution of conophylline and/or conophyllidine described so far increases the concentration of conophylline and/or conophyllidine in the blood in a short period of time; increases the weight of β cells, namely, proliferates β cells; reduces blood glucose levels; and elevates the insulin level Therefore, the water-soluble compositions of conophylline and/or conophyllidine described so far can be used for food compositions (for example, health foods, functional foods, foods for specified health uses, supplementary foods, etc.), and/or pharmaceutical compositions (for example, preparations for oral administration etc.) which are useful in growing β cells, reducing blood glucose levels, elevating insulin levels, and preventing or improving diabetes. Moreover, since weak acid to neutral water-soluble compositions can be ingested orally, they are capable of improving the insulin-producing abilities of patients having diabetes with decreased insulin-producing ability or being at risk of diabetes and recovering/maintaining them at normal levels, without performing painful treatments such as organ transplantations and injections, Here, the water-soluble composition of conophylline and/or conophyllidine is not limited to any specific type of composition as long as it contains conophylline and/or conophyllidine and can be prepared into an aqueous solution of conophylline and/or conophyllidine when mixed with water. Examples of this water-soluble composition include acidic aqueous solutions or neutral aqueous solutions of conophylline and/or conophyllidine and freeze-dried powders of these aqueous solutions.

The water-soluble composition according to the present invention may further contain antioxidants such as vitamin A, C, E, and polyphenol for improved stability of the solution, and a food additive, a flavoring agent, etc. for the purpose of adjustment of taste and/or flavor.

Furthermore, when the symptoms of diabetes develop, the body is always in the condition of hyperglycemia and in vivo glucose toxicity associated with hyperglycemia increases the oxidative stress. Pancreatic β cells have a particularly high sensitivity to oxidative stress; once pancreatic β cells have been regenerated by the effect of conophylline and/or conophyllidine, the regenerated cells are inferred to be continuously affected by an oxidative stress. It is therefore particularly important to maintain blood glucose levels at a normal level as much as possible, for the purpose of increasing the effect of conophylline and/or conophyllidine. For that purpose, it is preferred to administer some other blood glucose level-reducing agent such as a glucosidase inhibitor, biguanides, thiazolidines, a sulfonylureas; in vivo oxidative stress-reducing agents such as vitamins A, C or E, or polyphenol etc. simultaneously with conophylline and/or conophyllidine rather than to administer conophylline and/or a conophyllidine alone. Combined use with other blood glucose-reducing agent or antioxidant makes it possible to regenerate pancreatic β cells with a lower dose of conophylline and/or conophyllidine.

==Storage of Conophylline and/or Conophyllidine==

Degradation of conophylline and/or conophyllidine can be prevented by storing them shielded from light, regardless of storage temperature. Therefore, aqueous solutions, water-soluble compositions, food compositions, pharmaceutical compositions, etc. containing conophylline and/or conophyllidine according to the present invention can be stored at room temperature by shielding them from light. Moreover, the aforementioned aqueous solutions, water-soluble compositions, food compositions, pharmaceutical compositions, etc. can be efficiently prepared in a dark place.

EXAMPLES

The present invention will be more specifically described by giving examples hereinbelow. However, the scope of the present invention is not limited to these examples. It should be noted that purification and analysis of conophylline and/or conophyllidine were performed as follows.

1. Purification of Conophylline and/or Conophyllidine

Leaves of *Tabernaemontana divaricata*, harvested on Miyako-jima, Okinawa, were dried in a warm-air dryer at 60° C. for 16 h. From about 4 kg of the dried leaves obtained, conophylline (500 mg) and conophyllidine (100 mg) were purified through ethanol extraction, acid lysis, ultrafiltration (molecular weight cut-off 10000), purification by reversed-phase open column chromatography, and purification process by reversed phase HPLC. Since the purity of each purified product thus obtained was proved to be 99% or higher by LC/MS analysis, these purified products were used as reference materials in the following Examples. The molar absorption coefficient of conophylline in ethanol was found to be $\epsilon(335\ nm)=32,100$ as a result of analysis. For the molar absorption coefficient of conophyllidine, the literature data of $\epsilon(335\ nm)=12,300$ was used (Kam et al., J Nat Prod, 56, 1865-1871, 1993).

2. Method for Analyzing Conophylline and Conophyllidine

Conophylline and conophyllidine were analyzed by reversed phase HPLC in a high pressure gradient mode using a YMC-Pack Pro C18 RS column (4.6 mm×250 mm; manufactured by YMC Co., Ltd.). The mobile phase consisted of 1% by volume acetic acid as solvent A and acetonitrile as solvent B. The gradient program was set to start with 10% B at a flow rate of 1 ml/min, and the portion of B was increased linearly to 55% over 25 min. The column temperature was 40° C. and UV absorption was monitored at the wavelength of 335 nm. The reference solutions of conophylline and conophyllidine were prepared immediately before measurement and their concentrations were calculated from the absorbance at 335 nm of the solutions prepared.

Example 1

The following experiments were performed to examine the effects of oral administration of crude extract on blood glucose and insulin levels of diabetic model animals.
(1) Housing Conditions Thirty rats (Crj:CD(SD)IGS, SPF, male) purchased at 5 weeks old were acclimated for one week. Specifically, the rats were housed in an animal room with controlled temperature (20 to 26° C.), relative humidity (40 to 70%), ventilation (10 to 20 air changes/hour), and light (12 hour light period, 7:00 to 19:00). Solid chow (Funabashi Farm) and tap water were provided ad libitum.
(2) Induction of Diabetes and Grouping The acclimated rats were fastened for 24 hours and received an intraperitoneal injection of streptozotocin (hereinafter abbreviated as "STZ") at a dose of 60 mg/kg. The blood glucose level at 24 hours after administration of STZ was measured using a freestyle Kissei meter (C-D036-01014, Kissei Pharmaceutical Co., Ltd.). The animals whose blood glucose levels were 250 mg/dl or more were regarded as diabetic rats and used for the experiment, divided into 3 groups by the computer-assisted complete random sampling method (n=8 per group).
(3) Preparation and Administration of Test Substances Leaves of *Tabernaemontana divaricata*, harvested on Miyako-jima, Okinawa, were dried in a warm-air dryer at 60° C. for 16 h to yield dried leaves. 300 g of the dried leaves obtained was pulverized with a home mill. By adding 3 L of 60% ethanol to the pulverized product, conophylline and conophyllidine were extracted. The supernatant obtained by centrifugation was removed, 3 L of 60% by volume ethanol was added to the precipitant again for extraction and the supernatant was recovered. The supernatants were mixed, the ethanol was removed from the mixed supernatant by concentration on an evaporator, and the resulting solution was freeze-dried to afford about 50 g of dried product (Crude extract 1).

One drop of Tween 80 and then 10 ml of water for injection were added to 0.4 g of crude extract and the extract was suspended. This suspension was daily administered to the rats using a sonde by forced oral administration at a dose of 5 ml/kg body weight kg (200 mg/kg-administered group). In this group, the doses of conophylline and conophyllidine were 0.46 mg/kg/day and 0.32 mg/kg/day, respectively. Likewise, a suspension prepared by adding one drop of Tween 80 and 10 ml of water for injection to 0.1 g of the crude extract was daily administered to another group (50 mg/kg-administered group). In this group, the doses of conophylline and conophyllidine were 0.11 mg/kg/day and 0.08 mg/kg/day, respectively. Further, 10 ml of water for injection to which one drop of Tween 80 was added was daily administered to the control group. All the test substances were prepared immediately before administration every day.
(4) Measurement of Blood Glucose and Insulin Levels Blood glucose levels were measured at intervals of five days after the starting day of administration of each test substance. For measurement of blood glucose levels, animals were fasted for 16 hours from the previous day to the measurement. Blood was taken from the caudal vein and blood glucose levels were measured using FreeStyle Kissei Meter (C-D036-01014, Kissei Pharmaceutical Co., Ltd.). After measuring the blood glucose levels at day 15, the whole blood was taken from the abdominal aorta and serum was isolated by centrifugation. Insulin in these samples was analyzed using rebis insulin-rat T type (Shibayagi Co. Ltd.)
(5) Measurement of the Weight of β Cells The pancreas was removed and weighed on the day following the final day of administration. The pancreas was then fixed in 10% formalin and 4 μm paraffin sections were prepared according to the conventional method. Labeling of pancreas β cells were performed by immunohistochemistry staining based on the Labeled Strepto-Avidin Biotin method (DAKO LSAB+/HRP kit and Code No. K0690, Dako Cytomation), using anti-insulin (anti-insulin H-86, Code No. sc9168, Santa Cruz Biotechnology Inc., ×100) as the primary antibody and anti-rabbit Ig (Code No. E0353, Dako Cytomation, ×400) as the secondary antibody. For image analysis, in the images of the sections of all samples stained immunohistochemically with anti-insulin, which were digitalized through a film scanner (PrimeFilm 18001, Pacific Image Electronics), the areas of the cross sections of the pancreas were measured using NIH Image PPC Ver. 1.62 (Wayne Rusband, NIH). Further, in the digitalized images of all the β cell regions on each section using EclipseE600 and COOLPI X Microsystem (Nikon) with an object lens magnification of 10×, the areas of the β cell regions were measured using NIH Image PPC Ver. 1.62. From the result obtained, the weight of the β cells (mg) was calculated according to the formula presented below. The weights of the β cells inside and outside the islets of Langerhans (i.e., β cells solitarily identified in the regions without islets of Langerhans such as inside the acinus, in the ductal epithelium or around the duct) were separately measured in the analysis. In Table 1, total weights of the β cells are shown.

Formula: Number of β cells(mg)=pancreatic weight (mg)×area of β cell region(mm$^2$)/pancreatic cross section(mm$^2$)

(6) Statistical Approach

The Student-t-test was performed for significance relative to the control group.

Figure 2:
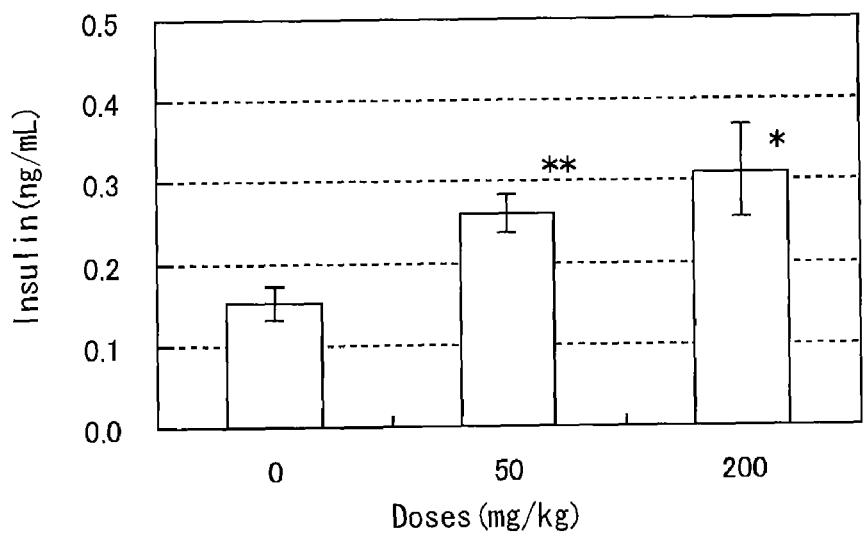
FIG. 2 is a graph showing the blood insulin levels after Crude extract I was continually administered to STZ rats for 15 days in one embodiment of the present invention. The vertical lines shows standard errors and the asterisks and double asterisks indicate having statistical significance of 5% and 1% relative to the control group, respectively.

FIG. 1 shows changes in the blood glucose levels during oral administration of Crude extract I for 15 consecutive days and FIG. 2 shows insulin levels after 15 days.
(7) Results

TABLE 1

| | Weight of the β cells (mg) | | |
| --- | --- | --- | --- |
| Group | Outside Langerhans' islets | Inside Langerhans' islets | Total |
| Control | 0.0196 ± 0.0046 | 0.2008 ± 0.0285 | 0.2204 ± 0.0293 |
| 50 mg/kg | 0.0351 ± 0.0074 | 0.2675 ± 0.0636 | 0.3026 ± 0.0702 |
| 200 mg/kg | 0.0491 ± 0.0125 | 0.2719 ± 0.1238 | 0.3210 ± 0.1356 |

As indicated in Table 1, the weight of β cells increased dose-dependently for any case of the total weight and those inside and outside the islets of Langerhans. Further, as shown in FIGS. 1 and 2, the administration of the test substance caused a dose-dependent decrease in the blood glucose levels and a dose-dependent increase in insulin levels. No difference was found in body weight between the administration groups and the control group.

Example 2

After some of the dried leaves obtained in Example 1 were pulverized in a mill, 10 g of the pulverized product was extracted with 100 ml of 60% ethanol. Then, the extract was centrifuged and supernatant containing conophylline and conophyllidine was recovered. Their concentrations were found to be about 33 μg/ml and 27 μg/ml, respectively. The supernatant was dispensed in 3 ml aliquots into 5 centrifuge tubes and then concentrated to dryness by centrifugation. A buffer (citric acid aqueous solution or sodium citrate buffer) at pH 2.6 to pH 6.0 prepared by appropriately mixing 0.1 M citric acid solution and 0.1 M sodium citrate solution was added at 0.1 ml per tube. After 10 min vigorous stirring, the supernatant was centrifugated again and diluted 10-fold with 50% ethanol. After the dilution, insoluble matter was removed by filtration with a 0.2-μm membrane filter and the contents of conophylline and conophyllidine in the filtrated supernatant were measured by HPLC (Table 2).

TABLE 2

| Solution | pH | Conophylline (mg/ml) | Conophyllidine (mg/ml) |
| --- | --- | --- | --- |
| Citric acid | 2.6 | 1.072 | 0.786 |
| Citrate buffer solution | 3 | 0.866 | 0.612 |
| Citrate buffer solution | 4 | 0.093 | 0.055 |
| Citrate buffer solution | 5 | 0.0018 | 0.0017 |
| Citrate buffer solution | 6 | 0.0009 | 0.0010 |

As indicated in Table 2, conophylline and conophyllidine were dissolvable in the aqueous solution having a pH equal to 3.0 or less and, even at pH 4.0, a small quantity of conophylline and conophyllidine dissolved.

Example 3

Next, extraction experiment was conducted using various solvents. 2 mg to 100 mg of the weighed pulverized product of dried leaves obtained by the same method as in Example 2 was extracted with 1 ml of each solvent shown in Table 3 by stirring for 10 minutes at room temperature or 50° C. and then pH of the each extract was measured. It should be noted that he solvents used were 0.1 N hydrochloric acid, 0.1 M citric acid, 0.1 M sodium citrate buffer solution (pH 3.0), 0.3 M acetic acid, a 90:10 mixture of 0.1 M citric acid and ethanol, and a 80:20 mixture of the same.

Then, the debris was removed from the extract by centrifugation and the amounts of conophylline and conophyllidine in the resulting solutions were measured by HPLC (Table 3).

TABLE 3

| Solvent | Temperature | Amount of solvent added (fold) | Post-extraction pH | Conophylline (mg/g) | Conophyllidine (mg/g) |
| --- | --- | --- | --- | --- | --- |
| 0.1M Citric acid | Room temperature | 10 | 2.7 | 0.09 | 0.05 |
| 0.1M Citric acid | Room temperature | 25 | 2.7 | 0.18 | 0.11 |
| 0.1M Citric acid | 50° C. | 25 | 2.7 | 0.32 | 0.17 |
| 0.1M Citrate buffer (pH 3.0) | Room temperature | 10 | 3.0 | 0.02 | 0.01 |
| 0.1M Citrate buffer (pH 3.0) | 50° C. | 25 | 30 | 0.25 | 0.14 |
| 0.1N Hydrochloric acid | Room temperature | 500 | 1.0 | 0.18 | 0.50 |
| 0.1N Hydrochloric acid | Room temperature | 250 | 1.1 | 0.24 | 0.58 |
| 0.1N Hydrochloric acid | Room temperature | 100 | 1.2 | 0.22 | 0.54 |
| 0.1N Hydrochloric acid | Room temperature | 50 | 1.2 | 0.24 | 0.47 |
| 0.1N Hydrochloric acid | Room temperature | 25 | 1.4 | 0.23 | 0.42 |
| 0.1N Hydrochloric acid | Room temperature | 10 | 1.5 | 0.11 | 0.10 |
| 0.3M Acetic acid | Room temperature | 50 | 2.7 | 0.37 | 0.20 |
| 0.1M citric acid + 10% ethanol | Room temperature | 25 | 2.7 | 0.34 | 0.23 |
| 0.1M citric acid + 20% ethanol | Room temperature | 25 | 2.7 | 0.35 | 0.21 |

As indicated in Table 3, conophylline and conophyllidine were efficiently extracted with the aqueous solutions having a pH equal to 3.0 or less, and the extraction efficiency increased by increasing the ratio of the solvent to be added, raising extraction temperature, and adding a small quantity of ethanol.

Example 4

10 mg aliquots of the pulverized product of the dried leaves obtained by the same method as in Example 2 were removed into Eppendorf tubes. 1 ml of distilled water and 1 ml of hydrochloric acid (0.005 N to 1 N) were added to each tube and stirred at 50° C. for 15 min for extraction and the pH of the extracts was measured. Then, the debris was removed by centrifugation and the supernatant was neutralized by the addition of sodium hydroxide aqueous solution. Further, after an equal volume of ethanol was added, the contents of conophylline and conophyllidine were measured by HPLC (Table 4).

TABLE 4

| Hydrochloric acid concentration (N) | Post-extraction pH | Conophylline (mg/g) | Conophyllidine (mg/g) |
| --- | --- | --- | --- |
| 0 | 5.3 | 0.015 | 0.006 |
| 0.005 | 4.7 | 0.011 | 0.004 |
| 0.01 | 3.5 | 0.078 | 0.036 |
| 0.02 | 2.6 | 0.206 | 0.130 |
| 0.05 | 1.9 | 0.234 | 0.153 |
| 0.1 | 1.5 | 0.237 | 0.162 |
| 0.2 | 1.3 | 0.222 | 0.150 |
| 0.5 | 1.1 | 0.151 | 0.110 |
| 1 | 1.0 | 0.137 | 0.070 |

As indicated in Table 4, conophylline and conophyllidine were extracted efficiently when the concentration of hydrochloric acid was 0.01 N or higher, and the extraction efficiency was particularly favorable when the hydrochloric acid concentration was from 0.02 to 0.2 N.

Example 5

200 ml of 0.1 N hydrochloric acid was added to 4 g of pulverized product of the dried leaves obtained by the same method as in Example 2, which was then extracted at 50° C. for 30 min. After the debris was removed by paper filtration, the extract was ultrafiltrated with pencil-type module SLP-0053 manufactured by Asahi Kasei Corporation (molecular weight cut-off 10,000) and 165 ml of filtrate was recovered. The pH of the filtrate was adjusted by gradually adding sodium carbonate aqueous solution and the precipitate formed was recovered by centrifugation. The precipitate was then vacuum-evaporated to yield 70 mg of dried product. This dried product contained 9.8 µg of conophylline and 13.3 µg of conophyllidine per mg

Example 6

The extract was prepared and clarified by removing debris by paper filtration in the same method as in Example 5. Then 100 ml of the clarified extract was adjusted to pH 6.0 with sodium hydroxide aqueous solution. This solution was centrifuged (1,500×g, 5 min) to separate into a supernatant (centrifuged supernatant) and precipitate (centrifuged precipitate). Next, the precipitate was dissolved in an equal volume of 50% ethanol, and the amounts of the active ingredients (conophylline and conophyllidine) in the clarified extract, the centrifuged supernatant, and the centrifuged precipitate were measured by HPLC. Further, the amounts of the active ingredient in the supernatant (lysate) obtained by adding 200 ml of distilled water to 4 g of the pulverized product of the dried leaves of *Tabernaemontana divaricata* and heating at 50° C. for 30 min, followed by centrifugation at 1,500×g for 5 min were also measured by HPLC. The results are shown in Table 5.

TABLE 5

|  | Conophylline (µg/ml) | Conophyllidine (µ/ml) |
| --- | --- | --- |
| Lysate | 0.04 | 0.02 |
| Aqueous extract | 2.62 | 2.01 |
| Centrifuged supernatant | 2.22 | 1.41 |
| Centrifuged precipitate | 0.48 | 0.30 |
| UF debris | 2.39 | 2.19 |
| UF filtrate | 0.00 | 0.00 |

As indicated in Table 5, conophylline and conophylline were present for the most part in the centrifuged supernatant, whereas only a small amount of conophylline and conophyllidine was present in the precipitate.

Further, a sodium hydroxide aqueous solution was added to 1 ml of the above-described clarified extract to adjust pH to 6.0. This extract was treated with an ultrafiltration membrane USY-5 (molecular weight cut-off: 50,000), manufactured by Advantech Co., Ltd. and the filtrate which had passed through the membrane was recovered (UF filtrate). At the same time, the remaining component on the membrane was dissolved and recovered using 1 ml of 50% ethanol (UF debris), and the amounts of the active ingredients in the UF filtrate and UF debris were measured by HPLC (Table 5). As a result, no amount of conophylline or conophyllidine was not detected in the filtrate at all; almost all was present in the fraction which had not permeated through the ultrafiltration membrane.

Example 7

In this example, stability of a water-soluble composition containing conophylline and conophyllidine was examined.

0.1 M citric acid was added to the pulverized product of the dried leaves obtained by the same method as in Example 2, and stirred at 60° C. After insoluble matter was filtered off, the solution was neutralized to pH 6.0 with 0.1 N sodium hydroxide, dispensed in 1 ml aliquots into test tubes, and concentrated to dryness by centrifugation.

First, 1 ml of 50% ethanol was added to one of the test tubes to dissolve solid content. The solution was filtered through a 0.2 µm membrane filter, and then conophylline and conophyllidine were analyzed by HPLC.

Figure 3:
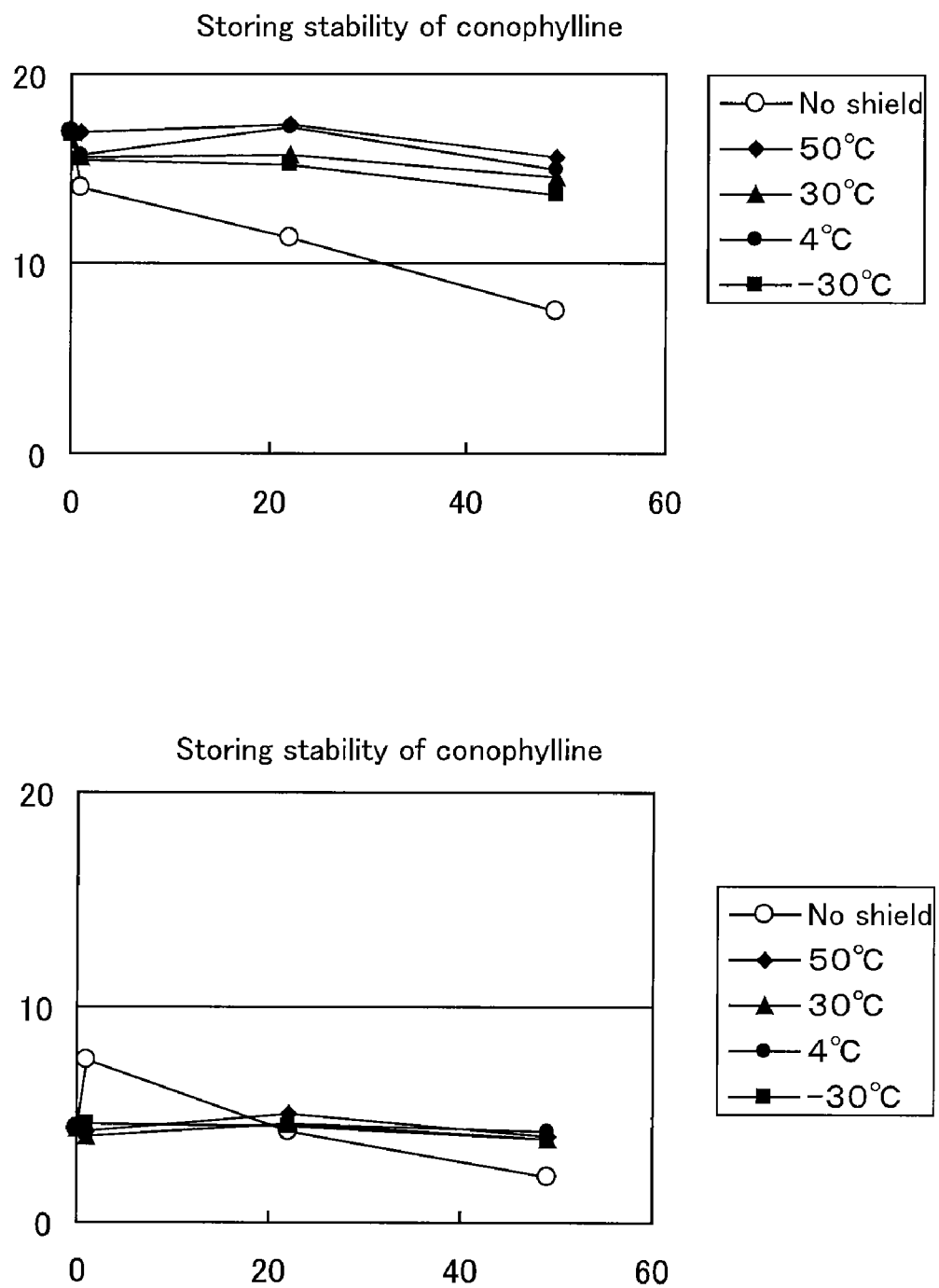
FIG. 3 is a graph showing the storing stability of the water-soluble composition containing conophylline and conophyllidine extracted with citric acid in one embodiment of the present invention.

Next, the remaining test tubes were divided into five groups, each of which being stored at −30° C. (shielded from light), 4° C. (shielded from light), 4° C. (not shielded from light), 30° C. (shielded from light), and 50° C. (shielded from light). After a lapse of a certain period of time, the composition was dissolved by addition of 50% ethanol, filtered, and analyzed by HPLC. The results are shown in FIG. 3. As indicated in FIG. 3, conophylline and conophyllidine were very stable irrespective of storage temperature when shielded from light, but were gradually decreased (degraded) when not shielded from light.

Example 8

This Example demonstrates that increases in blood conophylline and conophyllidine concentrations peak earlier when they are administered in extract than when administered in dried and pulverized leaves.

Dried leaves of *Tabernaemontana divaricata* were pulverized with a home mill, 1 g of the pulverized product was homogenized in 20 ml of 0.3 M acetic acid solution, and the active ingredient was extracted by stirring at 50° C. for 30 min. The supernatant was recovered by centrifugation and concentrated to dryness to obtain 0.3 g of powder (acetic acid extract). This powder contained conophylline and conophyllidine at 1.0 mg/g and 0.8 mg/g, respectively.

Further, 1 g of pulverized leaves was homogenized in 20 ml of distilled water and then concentrated to dryness to obtain 1 g of product (dried pulverized leaves). The amounts of the active ingredients of conophylline and conophyllidine were 0.40 mg/g and 0.35 mg/g, respectively.

Next, 0.2 g of the acetic acid extract and 0.5 g of the dried pulverized leaves were separately suspended in 5 ml of water for injection. These suspensions were administered to 5-week old healthy rats (Crj:CD (SD) IGS, SPF, male) using a sonde by forced oral administration at a dose of 5 ml/kg body weight (n=2 per suspension). Blood was taken from the orbital venous plexus of each rat before oral administration, 1.5, 3, 6, 12, and 24 hours post administration and serum was recovered by centrifugation. The concentrations of conophylline and conophyllidine in the blood were measured by precipitating protein by addition of 2 volumes of acetonitrile to the serum followed by HPLC analysis of the supernatant (Table 6).

TABLE 6

| Animal Number | Substance administered | Item analyzed | Before administration | Post-administration time (h) | | | | |
|---|---|---|---|---|---|---|---|---|
| | | | | 1.5 | 3 | 6 | 12 | 24 |
| 1 | Acetic acid extract | Conophylline | 0.000 | 0.324 | 0.196 | 0.122 | 0.029 | 0.001 |
| | | Conophyllidine | 0.000 | 0.040 | 0.016 | 0.011 | 0.001 | 0.000 |
| 2 | Acetic acid extract | Conophylline | 0.000 | 0.537 | 0.384 | 0.451 | 0.261 | 0.041 |
| | | Conophyllidine | 0.000 | 0.109 | 0.053 | 0.045 | 0.012 | 0.001 |
| 3 | Dried pulverized leaves | Conophylline | 0.000 | 0.186 | 0.234 | 0.523 | 0.242 | 0.060 |
| | | Conophyllidine | 0.000 | 0.017 | 0.019 | 0.028 | 0.008 | 0.001 |
| 4 | Dried pulverized leaves | Conophylline | 0.000 | 0.000 | 0.402 | 0.647 | 0.283 | 0.056 |
| | | Conophyllidine | 0.000 | 0.000 | 0.060 | 0.054 | 0.013 | 0.002 |

Unit: µg/ml

As indicated in Table 6, when the acetic acid extract was administered, the blood conophylline and conophyllidine concentrations reached their maximum in 1.5 hours after administration and then gradually decreased. In contrast, when the dried pulverized leaves were administered, the peak blood concentrations tended to be delayed a few hours.

Example 9

This Example demonstrates that the method for extracting conophylline and conophyllidine does not influence changes in the blood concentrations when they are administered orally.

One drop of Tween 80 was added to the crude extract (0.05 g) obtained in Example 1, which was suspended in 5-ml of water for injection. This suspension was administered to 5-week old rats (Crj:CD(SD) IGS, SPF, male) using a sonde by forced oral administration at a dose of 5 ml/kg body weight (n=2). Blood was taken from the orbital venous plexus of each rat at 0.5, 1, 2, 4, 8, 24 hours post administration and serum was recovered by centrifugation. Then, the concentrations of conophylline and conophyllidine in the blood were measured (Table 7) by the same method as in Example 8. As the control, water for injection containing one drop of Tween80 was administered orally at a dose of 5 ml/kg body weight (n=2) and the blood concentrations were measured in the same manner.

TABLE 7

| Animal Number | Substance administered | Item analyzed | Post-administration time (h) | | | | | |
|---|---|---|---|---|---|---|---|---|
| | | | 0.5 | 1 | 2 | 4 | 8 | 24 |
| 1 | Water for injection | Conophylline | 0 | 0 | 0 | 0 | 0 | 0 |
| | | Conophyllidine | 0 | 0 | 0 | 0 | 0 | 0 |
| 2 | Water for injection | Conophylline | 0 | 0 | 0 | 0 | 0 | 0 |
| | | Conophyllidine | 0 | 0 | 0 | 0 | 0 | 0 |
| 3 | Crude extract I | Conophylline | 0.398 | 0.472 | 0.403 | 0.515 | 0.329 | 0.108 |
| | | Conophyllidine | 0.054 | 0.061 | 0.040 | 0.036 | 0.024 | 0.013 |
| 4 | Crude extract I | Conophylline | 0.332 | 0.270 | 0.200 | 0.256 | 0.116 | 0.090 |
| | | Conophyllidine | 0.065 | 0.062 | 0.032 | 0.025 | 0.013 | 0.009 |

Unit: µg/ml

As indicated in Table 7, the changes in the blood concentrations of oral-administered conophylline and conophylline extracted using hydrous alcohol (Crude extract I) were found to be almost the same as those of the acetic acid extract. Thus conophylline and conophyllidine are transported into blood to a similar degree in both cases; therefore, it can be judged that there is no difference in oral effect between administration of an extract prepared with alcohol and administration of an extract prepared with acidic solution.

Example 10

This Example demonstrates that the amounts of conophylline and conophyllidine dissolving in an aqueous solution after neutralization increases by adding an anionic water-soluble macromolecule to an acidic aqueous solution containing conophylline and/or conophyllidine partially purified by fractionation. Here, an experiment was conducted by using hydrochloric acid and pectin as an acidic aqueous solution and an anionic water-soluble macromolecule, respectively.

10 mg of the dried product obtained in Example 5 was dissolved in 5 ml of 0.1 N hydrochloric acid. This solution was dispensed in 0.5 ml aliquots into test tubes. Then, 10 µl or 100 µl of a 0.25% aqueous solution of pectin (Genue pectin type YM-150-LJ) was added and filled up to a total volume of 2 ml with distilled water. Meanwhile, only distilled water was added to some of the test tubes in a total volume of 2 ml.

Subsequently, the solution, after being adjusted to pH 6.0 with sodium carbonate aqueous solution, was filled up to a total volume of 2.5 ml and was centrifuged at 5,000×g for 10 min. The supernatant was recovered and the concentrations of conophylline and conophyllidine were measured. Meanwhile, the concentrations of conophylline and conophyllidine in the solutions, which was made by filled up to a total volume of 2.5 ml only with distilled water, were also measured as the control. The result is shown in Table 8.

TABLE 8

| | Amount of pectin added (µg/ml) | | | |
|---|---|---|---|---|
| | 0 | 10 | 100 | Control |
| Conophyllidine (µg/ml) | 1.5 | 2.2 | 3.0 | 4.6 |
| Conophylline (µg/ml) | 1.5 | 2.1 | 2.6 | 3.7 |

Thus, by adding pectin to hydrochloric acid containing conophylline and conophyllidine, the amounts of conophylline and conophyllidine dissolving after neutralization increased with the amount of pectin added.

Example 11

In this example, a similar experiment to that described in Example 10 was performed using conophylline and conophyllidine partially purified by ethanol extraction.

Crude extract (250 mg) obtained in Example 1 was dissolved in 5 ml of 0.1 N hydrochloric acid. Then, after insoluble matter was removed by centrifugation (1,500×g, 5 min), the solution was dispensed in 0.5 ml aliquots into test tubes. Then, 10 µl or 100 µl of a 0.2% aqueous solution of pectin (Genue pectin type YM-150-LJ) or 0.2% aqueous solution of sodium polyacrylate (degrees of polymerization=30,000 to 40,000, manufactured by Wako Pure Chemical Industries, Ltd.) was added and filled up to a total volume of 2 ml with distilled water. Meanwhile, only distilled water was added to some of the test tubes in a total volume of 1.9 ml (without an additive).

Subsequently, the solution, after being adjusted to pH 6.0 with sodium carbonate aqueous solution, was filled up to a total volume of 2 ml and was centrifuged at 5,000×g for 10 min. The supernatant was recovered and the concentrations of conophylline and conophyllidine were measured. Meanwhile, the concentrations of conophylline and conophyllidine in the solutions, which was made by filled up to a total volume of 2.5 ml only with distilled water, were also measured as the control. The result is shown in Table 9.

TABLE 9

| Additive | None | Pectin | | Sodium polyacrylate | | Control |
|---|---|---|---|---|---|---|
| Concentration (µg/ml) | — | 10 | 100 | 10 | 100 | — |
| Conophylline (µg/ml) | 2.52 | 1.74 | 3.83 | 1.87 | 4.85 | 8.42 |
| Conophyllidine (µg/ml) | 3.27 | 2.42 | 5.19 | 2.50 | 8.45 | 11.83 |

Like in Example 10, by adding pectin or sodium polyacrylate, the concentrations of the conophylline and conophyllidine in the supernatant after neutralization increased.

Example 12

In this Example, a similar experiment to that described in Example 10 was performed using conophylline and conophyllidine partially purified by reversed phase column chromatography.

Crude extract I (250 mg) obtained in Example 1 was dissolved in 5 ml of ethanol. Water was added to this solution in a total volume of 50 ml, which was passed through a glass column packed with about 5 ml of ODS resin (DM1020T, manufactured by Fuji Silysia Chemical Ltd.). After unadsorbed matter was removed by washing the column with 10 ml of distilled water, the adsorbed component was eluted with 10 ml of ethanol. Then, after the solvent was removed by centrifugal concentration, the concentrate was dissolved in 5 ml of 0.1 N hydrochloric acid and the solution was dispensed in 0.5 ml aliquots into test tubes. Then, 10 µl, 100 µl, or 1000 µl of a 0.2% aqueous solution of pectin or 0.2% aqueous solution of sodium polyacrylate was added to the aliquots. The solutions were treated in the same way as in Example 11 and the concentrations of conophylline and conophyllidine in the supernatants were measured. The results are shown in Table 10.

TABLE 10

| Additive | None | Pectin | | | Sodium polyacrylate | | Control |
|---|---|---|---|---|---|---|---|
| Concentration (µg/ml) | — | 10 | 100 | 1000 | 10 | 100 | — |
| Conophylline (µg/ml) | 0.19 | 0.27 | 0.55 | 2.59 | 0.24 | 5.15 | 11.28 |
| Conophyllidine (µg/ml) | 0.16 | 0.13 | 0.57 | 2.74 | 0.17 | 6.99 | 16.08 |

Although the solubilities of neutralized conophylline and conophyllidine partially purified by reversed-phase column chromatography were substantially reduced, the addition of pectin or sodium polyacrylate increased the solubilities of conophylline and conophyllidine, like in Example 10 and 11.

Further, it was confirmed that although the anionic water-soluble macromolecule has no effect on the solubility of conophylline or conophyllidine when it merely coexists with conophylline and/or conophyllidine, it can increase the solubilities of conophylline and conophyllidine when conophylline and/or conophyllidine are dissolved in acidic aqueous solution followed by neutralization. Examples of the anionic water-soluble mavromolecule that exhibits such an effect include pectin and polyuronic acid as well as polyacrylic acids (e.g., alginic acid etc.) Anionic water-soluble macromolecules having no carboxyl group, such as sodium polyphosphate, did not exhibit the aforementioned effect.

Example 13

This Example demonstrates that the solubilities of conophylline and conophyllidine increased by the addition of a surface active agent to a hydrophilic solvent, 10 mg of weighed Crude extract I obtained in Example 1 was added to 1 ml of distilled water or 1 ml of 1% sodium dodecyl sulfate (SDS) aqueous solution and was stirred vigorously. The solution was centrifuged at 5,000×g for 2 min and the concentrations of conophylline and conophyllidine in the supernatant were measured. The results are shown in Table 11.

TABLE 11

|  | Conophylline (μg/ml) | Conophyllidine (μg/ml) |
| --- | --- | --- |
| Distilled water | 0.39 | 0.68 |
| 1% SDS | 2.61 | 2.97 |

As indicated in Table 11, conophylline or conophyllidine hardly dissolved in distilled water, but their solubilities increased by the addition of a surface active agent.

Example 14

In this example, the effect of conophylline and/or conophyllidine on fasting blood glucose levels of heredity diabetic model rats was examined.
(1) Animal Housing Conditions Sixty Goto-Kakizaki (GK) rats (male, 5 weeks of age), an animal model of hereditary diabetes, were housed under the same conditions as in Example 1. Random blood glucose levels were monitored by the same procedure as in Example 1. As a result, an increase was noted in the random blood glucose levels at 11 weeks of age. Accordingly, the rats were regarded as diabetic rats based on the blood glucose levels at 11 weeks of age and used for the following experiments.
(2) Preparation of the Test Substance Leaves of *Tabernaemontana divaricata*, harvested on Miyako-jima, Okinawa, were dried in a warm-air dryer at 60° C. for 16 hours to obtain dried leaves. 5 kg of the dried leaves was added to 250 L of 0.025 N hydrochloric acid whose temperature had been raised to 50° C. and the resulting mixture was stirred for 30 min. Subsequently, the leaf debris was removed by passing the mixture through a metal mesh, followed by filtration with a basket centrifugal filter to recover filtrate (clear aqueous extract).

A 20 L-volume stainless column was packed with a synthetic adsorption resin Amberlite XAD16-HP (manufactured by Organo Co. Ltd.) and washed thoroughly with water. Then, all of the above-mentioned aqueous extract was passed through the column at 100 L/h. The column was sequentially washed with 100 L of water and 100 L of 30% ethanol aqueous solution and the component adsorbed onto the resin was eluted with 100 L of pure ethanol. By concentrating and drying the resulting eluate, a powdered composition containing conophylline and conophyllidine was obtained.

The above-described pasty composition was dissolved in the 0.1 M citric acid aqueous solution and then adjusted to pH 6.0. The resulting precipitate was recovered by centrifugation and vacuum evaporated to obtain powder containing 14 mg/g and 15 mg/g of conophylline and conophyllidine, respectively (Crude extract II).
(3) Absorbance of Crude Extract II Prior to administration of the test substance, the Crude extract II absorption test was performed in the GK rats which did not have a large elevation in random blood glucose levels. Sixteen 10-week old GK rats were divided into four groups (n=4 per group). Two groups (the fasted groups) were fasted for 16 hours, and the remaining two groups (the fed groups) were allowed ad libitum access to chow and water. The fed groups received Crude extract II (containing Tween 80) at 4.3 mg/kg or 13 mg/kg. Blood was taken at 1.5, 3, 6, 12, and 24 hours post administration and plasma conophylline concentration was measured. Likewise, the fasted groups also received Crude extract II and plasma conophylline concentration was measured. The results are shown in FIG. 4.

Figure 4:
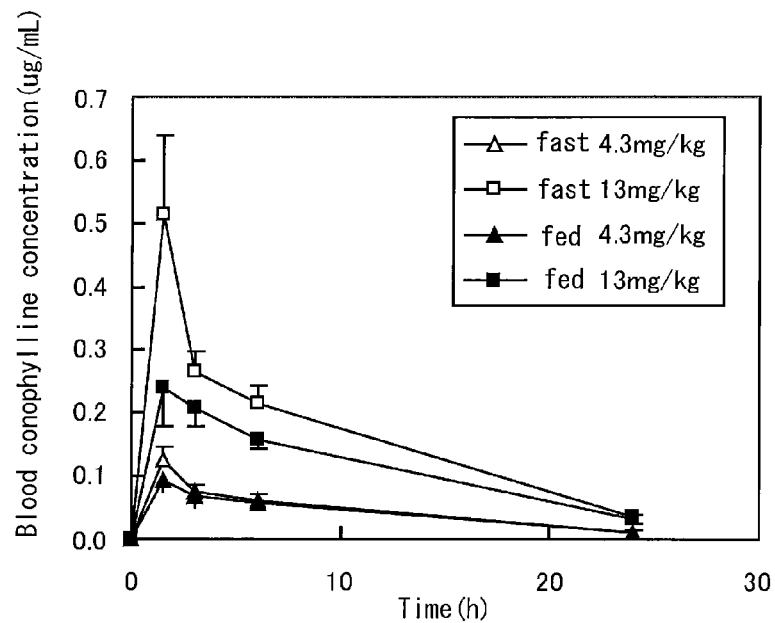
FIG. 4 is a graph showing the results of the absorption test of Crude extract II using GK rats which random blood glucose levels do not elevate so much in one embodiment of the present invention.
Figure 5:
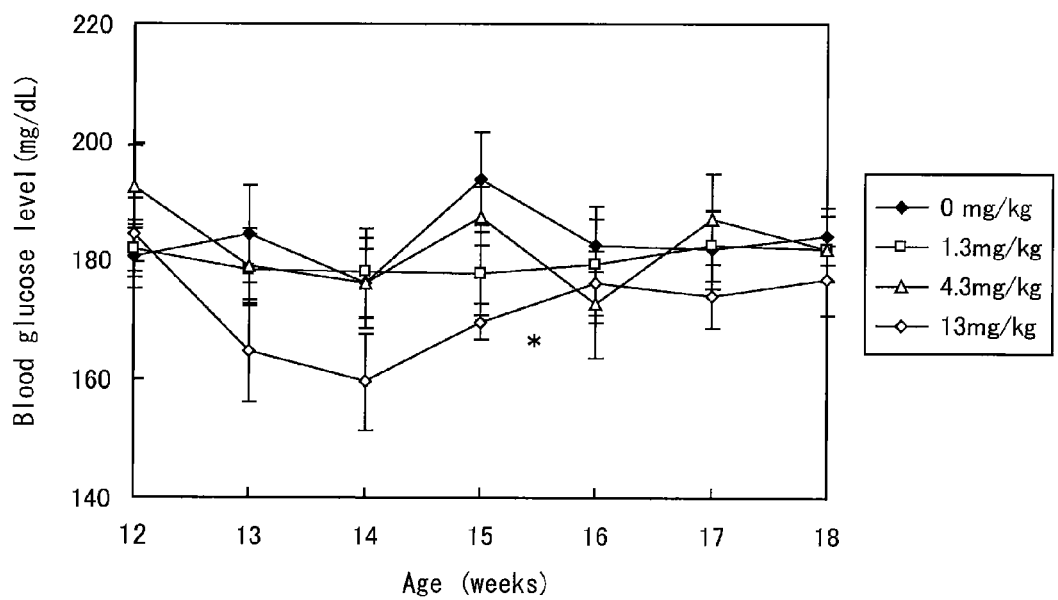
FIG. 5 is a graph showing the changes in random blood glucose levels of GK rats to which Crude extract II was continually administered in various dosages in one embodiment of the present invention. The vertical lines shows standard errors and the asterisks indicate having statistical significance at the 5% significance level relative to the control group.
Figure 6:
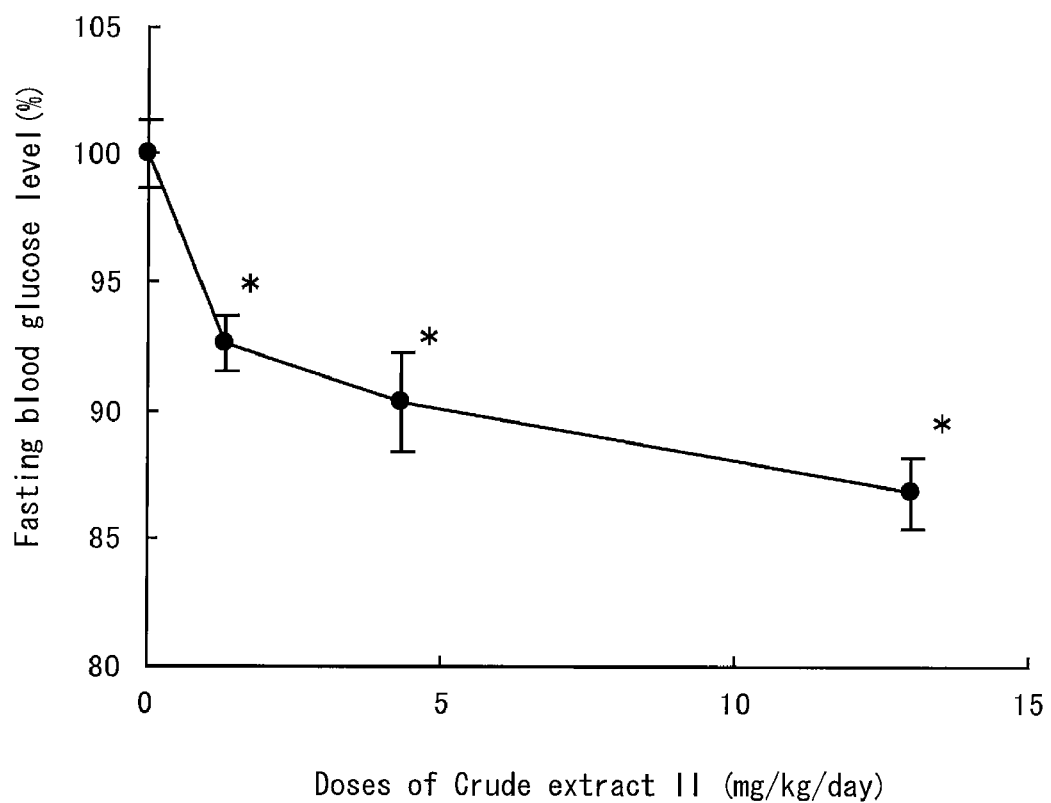
FIG. 6 is a graph showing the changes in fasting blood glucose levels of GK rats to which Crude extract II was continually administered in various dosages in one embodiment of the present invention. The data are shown in relative values when the fasting blood glucose levels of control rats were taken as 100%. The vertical lines show standard errors and the asterisks indicate statistical difference at the 5% significance level relative to the control group.

As indicated in FIG. 4, the blood conophylline concentration was slightly higher in the fasted groups, but no significant difference was noted.
(4) Administration of the Test Substance Administration of Crude extract II to 12-week old diabetic rats was started using the same approach as in Example 1. The doses of the test substance administered were 0 mg/kg/day (control group; n=10), 1.3 mg/kg/day (low dose group; n=10), 4.3 mg/kg/day (mid dose group; n=10), and 13 mg/kg/day (high dose group; n=10). It was administered in the morning daily for 42 consecutive days.
(5) Measurement of Blood Glucose Levels Random blood glucose levels were measured at intervals of one week after the starting day of administration of the test substance (FIG. 5). Further, rats were fasted for 16 hours, starting from the evening of the final day of the administration of the test substance, and the blood glucose level (fasting blood glucose level) was measured in the next morning (FIG. 6). As indicated in FIG. 5, the random blood glucose levels, although varying, in the group receiving Crude extract II at 13 mg/kg were always lower than those in the control group throughout the treatment duration, and at 3 weeks (15 weeks of age) after the start of administration, they significantly decreased. Moreover, the fasting blood glucose levels of the 13 mg/kg-administered group decreased depending on the dose of Crude extract II, as indicated in FIG. 6.

In conclusion, it was shown that conophylline purified by using the method for purification according to the present invention is useful or effective as a food composition or a pharmaceutical composition when actually administered in vivo.

INDUSTRIAL APPLICABILITY

According to the present invention, aqueous solutions of conophylline and/or conophyllidine; methods for purifying conophylline and/or conophyllidine from the aqueous solutions, methods for producing the aqueous solutions; water-soluble compositions containing conophylline and/or conophyllidine useful for food compositions or pharmaceutical compositions or methods for producing the water-soluble compositions; and food compositions or pharmaceutical compositions containing the water-soluble compositions can be provided.

The invention claimed is:

1. A method for purifying conophylline and/or conophyllidine, comprising:
   the fractionation step of fractionating an extract of a plant producing conophylline and/or conophyllidine prepared with an acidic aqueous solution having a pH equal to or less than 4 at a molecular weight of 10000; and
   the recovery step of recovering the low-molecular-weight fraction obtained by the fractionation step.

2. The purification method of claim 1, further comprising:
   the neutralization step of neutralizing the low-molecular-weight fraction; and
   the recovery step of recovering a precipitate precipitated at the neutralization step.

3. A method for purifying conophylline and/or conophyllidine, comprising:
   the neutralization step of neutralizing an extract of a plant producing conophylline and/or conophyllidine prepared with an acidic aqueous solution having a pH equal to or less than 4;
   the fractionation step of fractionating the extract of the plant producing conophylline and/or conophyllidine prepared with an acidic aqueous solution having a pH equal to or less than 4 at a molecular weight of 50000; and
   the recovery step of recovering a high-molecular-weight fraction obtained by the fractionation step.

* * * * *